United States Patent
Gambaretto

Patent Number: 6,121,212
Date of Patent: Sep. 19, 2000

[54] LUBRICANT FOR IMPROVED GLIDING PROPERTIES OF SKIS AND ITS APPLICATION IN SKIING

[75] Inventor: Gian Paolo Gambaretto, I-Padova, Italy

[73] Assignee: Centeiro Trading LDA, Fuchal/Madeira, Portugal

[21] Appl. No.: 09/261,131

[22] Filed: Mar. 3, 1999

[30] Foreign Application Priority Data

Mar. 3, 1998 [CH] Switzerland ............... 0495/98

[51] Int. Cl.[7] ............................................. C10M 131/04
[52] U.S. Cl. ............................ 508/590; 570/134; 570/175; 570/176
[58] Field of Search ......................... 508/590; 570/134, 570/175, 176

[56] References Cited

U.S. PATENT DOCUMENTS

| | | | |
|---|---|---|---|
| 2,856,440 | 10/1958 | Wolff | 570/134 |
| 3,674,432 | 7/1972 | Margrave et al. | 23/205 |
| 3,698,731 | 10/1972 | Jost et al. | 280/11.136 |
| 3,902,732 | 9/1975 | Fosha, Jr. et al. | 260/11.136 |
| 4,118,532 | 10/1978 | Homsy | 428/294 |
| 4,272,577 | 6/1981 | Lyng | 428/116 |
| 4,321,295 | 3/1982 | Smith-Johannsen | 428/206 |
| 4,679,814 | 7/1987 | Meatto et al. | 280/610 |
| 4,703,075 | 10/1987 | Egami | 524/269 |
| 4,754,085 | 6/1988 | Gervasutti et al. | 570/175 |
| 4,933,127 | 6/1990 | Guiguet | 264/80 |
| 5,131,674 | 7/1992 | Tokui et al. | 570/134 |
| 5,202,041 | 4/1993 | Traverso et al. | 508/590 |
| 5,302,764 | 4/1994 | Sekiya et al. | 570/123 |
| 5,423,994 | 6/1995 | Traverso et al. | 570/134 |
| 5,530,169 | 6/1996 | Bielefeldt et al. | 570/175 |
| 5,648,568 | 7/1997 | Oharu et al. | 570/176 |
| 5,763,707 | 6/1998 | Scott et al. | 570/134 |
| 5,914,298 | 6/1999 | Karydas | 508/590 |

FOREIGN PATENT DOCUMENTS

| | | |
|---|---|---|
| 0 132 879 | 2/1985 | European Pat. Off. |
| 39 35 525 | 2/1991 | Germany |
| 403157494 | 7/1991 | Japan |
| 403157497 | 7/1991 | Japan |
| 1069089 | 5/1967 | United Kingdom |

OTHER PUBLICATIONS

English–language abstract No. 103:126307u of Jpn Kokai Tokkyo Koho JP 60 67, 593 (Apr. 17, 1985).
English–language abstract No. 103:126306t of Jpn Kokai Tokkyo Koho JP 60 67, 594 (Apr. 17, 1985).
English–language abstract No. 112:142609k of Jpn Kokai Tokkyo Koho JP 01,266,192 (Oct. 24, 1989).
English–language abstract No. 102:28136x of Jpn Kokai Tokkyo Koho JP 59,149,996(Aug. 28, 1984).
English–language abstract No. 6413q of German Patentschrift 1,594,392; Kometani et al. (Apr. 26, 1973).
English–language abstract No. 117:9136r of Jpn Kokai Tokkyo Koho JP 03,252,453 (Nov. 11, 1991).
English–language abstract No. 96:218846j of U.S.S.R. SU 899,597; Blank, et al. (Jan. 23, 1982).
English–language abstract No. 99:177002x of U.S.S.R. SU 1,031,993; Oleschchuk, et al. (Jul. 30, 1983).
English–language abstract No. 107:135568q of Jpn. Kokai Tokkyo Koho JP 62 54,753 (Mar. 10, 1987).

*Primary Examiner*—Jacqueline V. Howard
*Attorney, Agent, or Firm*—Hollander Law Firm, P.L.C.

[57] ABSTRACT

The present invention concerns a lubricant for improving the gliding properties of skis and its application to skiing. The lubricant possesses an elevated molecular weight but has a very low melting point. Furthermore, the lubricant does not crystallize easily and thus remains oily or waxy also at low temperatures. The lubricant is constituted of four perfluorinated chains attached to a hydrogenated core in a symmetrical arrangement in such a manner that a tetra-substituted derivative or tetrakis derivative is formed according to the following formula

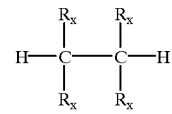

wherein each $R_x$ group can be the same or different and comprises a perfluorinated alkyl group.

20 Claims, No Drawings

LUBRICANT FOR IMPROVED GLIDING PROPERTIES OF SKIS AND ITS APPLICATION IN SKIING

The present invention concerns a lubricant for improving the gliding properties of skis, and its application in skiing for endowing skis with improved gliding properties.

The sole of skis are mostly made from high or medium density polyethylene and for improving the gliding properties lubricants (ski waxes) are applied, usually paraffins having a lower surface tension than the polyethylene.

Ski waxes of this type usually contain substances such as animal oils, vegetable oils, paraffin waxes, fatty acid alcohols, esters of alcohols and of fatty acids, and other chemical substances, generally applied in more or less complex blends.

In this field also agents of non-traditional types have been disclosed that provide the skis with gliding properties which are better in comparison to the traditional ski waxes. In particular in the European Patent No. 132 879 a solid agent is described for improving the skis gliding properties, which essentially is composed of linear perfluoroparaffins containing 10 to 20 atoms of carbon in the actual molecule and which can be applied also in blends with paraffin waxes and, more generally, with the traditional ski waxes. The inconvenience presented by these perfluorinated gliding agents generally consists in their poor compatibility with the paraffin waxes for which reason usually an agent is to be applied which favours such compatibility, in particular a fluorinated tensoactive substance.

Furthemore new blends were patented consisting of chains only partially fluorinated which are soluble in the ordinary paraffins: compare the German Patent No. 3925525 granted Feb. 7, 1991 to the Hoechst Company, in which the methods of synthesis are claimed of products of the type $R_f$-$R_H$-$R_G$ and the U.S. Pat. No. 5,202,041 dated Apr. 13, 1993 which describes the synthesis and the speed tests on snow of products of the type $R_f$-$R_H$.

Other patents exist by Asahi Glass and more specifically the Japanese Patents No. 03157497 and No. 03157494 of 1991 in which blends are claimed composed of: paraffins, fluoroalkanes and fluorographites.

The perfluoroparaffins known to be in use which provide a low surface tension and thus optimum sliding properties present, however, the following disadvantages:

High melting temperature even at relatively low molecular weighs, for example the compound $C_{16}$-$F_{34}$ melts at 125° C. and thus can not be applied to the ski sole alone without risk of paring or deformation of the latter.

Noticeable vapor pressure also in the solid state due to which slow evaporation can occur.

Insolubility in the sole material of the ski (usually consisting of high density polyethylene) due to which they can be absorbed physically merely on porous ski soles and not containing other types of paraffin waxes.

The blended waxes of the $R_f$-$R_H$ type and of the $R_f$-$R_H$-$R_f$ type are known first of all as tensoactive substances applied for taking up the perfluoroparaffins into the hydrocarbon paraffins.

They furthermore can be used all by themselves as their vapor pressures are much lower and thus also their melting points are much lower.

The advantage of the compounds according to the present invention compared to all compounds known according to the state of the art is seen in the following points:

Products of high molecular weight (and thus of reduced vapor pressure) but presenting a very low melting point (behaving practically like oils with low-melting waxes).

The molecular weight of the hydrogenated central core being much smaller compared to the four perfluorinated chains surrounding it the surface tension properties are practically identical to the ones of the perfluorinated paraffins.

Furthermore, owing to their spatial configuration they do not crystallize easily and thus remain oily liquids or low-melting waxes also at low ambient temperatures.

Expressed in other words, these products combine the best properties of the perfluoroparaffins (low surface tension and low coefficient of friction) with the ones of the compounds of the types $R_f$-$R_H$ and $R_f$-$R_H$-$R_f$ which present a high boiling-point, a low melting point and can be dissolved, even if partially only, in the hydrogenated paraffins.

The compound according to the present invention can be represented as tetra-substituted derivatives of ethane according to the following formula:

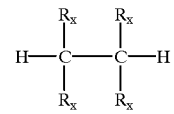

where $R_x$=$R_f$=$C_6F_{13}$, $C_8F_{17}$, $C_{10}F_{21}$, $C_{12}F_{25}$, or $R_x$=$R_fCH_2$=$C_6F_{13}CH_2$, $C_8F_{17}CH_2$, $C_{10}F_{21}CH_2$, $C_{12}F_{25}CH_2$, or $C_6F_{13}CH_2$—$CH_2$, $C_8F_{17}CH_2$—$CH_2$, $C_{10}F_{21}CH_2$—$CH_2$, $C_{12}F_{25}CH_2$—$CH_2$, wherein $R_f$ is a perfluorinated alkyl group.

The path of synthesis of these products can be the following:

1)

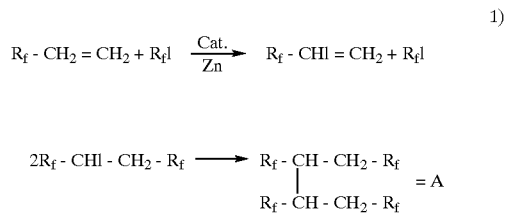

where A=1,2,3,4-Tetracis(perfluoralkyl)butane

2)

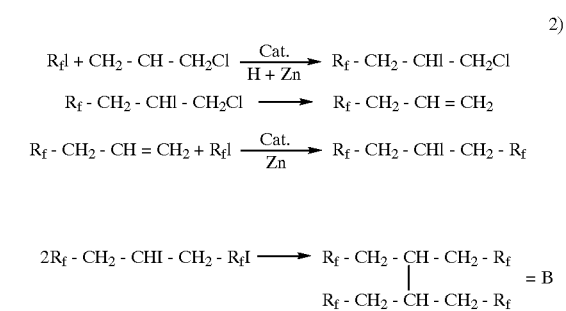

where B=1,1-2,2-Tetrakis(perfluoralkyl-methylene)ethane and where the chain $R_f$=$C_4F_9$, $C_6F_{13}$, $C_8F_{17}$, $C_{10}F_{21}$, $C_{12}F_{25}$.

In the following some practical examples are described of the manufacture of the products according to the present invention.

EXAMPLE NO. 1

Synthesis of the Tetracis 1,2 Perfluorohexyl-1,2-Perfluorohexylmethylethane or 1,2,3,4-Tetrakis (Perfluorohexyl)Butane, Compound (A)

In a small autoclave of 250 cubic centimeters capacity 65 grams of $C_6F_{13}$—CH $CH_2$ (0.19 moles), 179 grams of $C_6F_{13}$I (0.39 moles) and 4 grams of azobisisobutyronitril are placed.

After refrigerating the whole mixture to −40° C. the autoclave, in which a slight vacuum is established first, purged with repeatedly using $N_2$.

The autoclave thereupon is closed and the temperature gradually is brought to 80° C. and is maintained at this level during 8 hours using a thermostatic bath.

After cooling down, the autoclave is emptied and 229 grams of a blend is removed containing, according to chromatographic analysis, merely 19 percent of the weight of the pre-product material.

These 229 grams first are subjected to a distillation process at atmospheric pressure and the distillation is stopped when the heated vessel reaches 180° C. In the first process, 169 grams are collected of the top product in the head, whereas about 60 grams remain in the heating vessel.

These 60 grams thereupon are subjected to a distillation process under vacuum at an absolute pressure of 25 mm Hg.

At 114° C. in the heating vessel and 77° C. in the head the distillation process is started, and it is stopped when a temperature of 120° C. in the heating vessel is reached.

At this stage 52 grams of a viscous semi-solid liquid are collected which according to chromatographic analysis contains 93.2% $C_6F_{13}$—CHI—$CH_2$—$C_6F_{13}$—(B).

Subsequently in a neck round bottom flask four equipped with an agitator, a thermometer, a droplet funnel and a coolant cycle, 120 cubic centimeters of acid anhydride and 20 grams of Zn are placed, the whole mixture being brought to a temperature of 70° C. using a thermostatic bath. The infeed of droplets then is started of the 52 grams of B, which is rendered fluid by warming to 55 to 60° C.

After 15 minutes the infeed process is finished and the temperature of 70° C. is maintained for 2 hours in the flask. The end of the reaction is monitored using gas-chromatographic analysis.

After cooling the whole mixture is emptied in water and ice and organic phase is separated after 50 cubic centimeters of methylene chloride have been added.

The separated organic phase is subjected to a distillation process and after recovery of the methylene chloride under atmospheric pressure the final product (A) is distilled off at 185° to 190° C. under a vacuum of 745 mm Hg. In this manner 46 grams of the product at 96 percent purity are obtained.

EXAMPLE NO. 2

Synthesis of 1,1-1,2 (Tetrakisperflourohexylmethylene)ethane, Compound B a) Preparation of the $C_6F_{13}$—$CH_2$—CHI—$CH_2$Cl In an autoclave of 1 liter capacity 525 grams of $C_6F_{13}$I, 7.5 grams of azobisisobutyronitrile and 160 grams of allyl chloride are placed.

After purging with nitrogen the autoclave is closed and placed into a thermostatic bath. The temperature of the autoclave is gradually brought up to 80° C., and is maintained for 8 hours.

After cooling down the autoclave is emptied and by means of a distillation process the excess allyl chloride is removed along with unreacted $C_6F_{13}$I. In the heating vessel 430 grams of the product are obtained at 85 percent purity.

a) Preparation of the olefin $C_6F_{13}$—$CH_2$—CH=$CH_2$

To the 430 grams remaining in the heating vessel 750 cubic centimeters of ethanol and 150 cubic centimeters of 35% HCl are added.

The whole mixture is placed in a spherical vessel equipped with a thermostat, a mechanical agitator, a coolant cycle and an opening for adding Zn in powder form.

After heating the whole mixture to 35° C. the feeding of Zn in powder form is started while the temperature is controlled so as not to exceed 40° C. In this manner 70 grams of Zn powder are added in the course of about one hour.

After two additional hours of agitation at the constant temperature the whole mixture is emptied into a separator funnel and 310 grams of a white colourless liquid are obtained containing about 73 percent of the desired product.

By means of fractional distillation 215 grams of 98.5 percent pure $C_6F_{13}$—$CH_2$CH=$CH_2$ with a boiling interval of 118° to 120° C. are obtained.

c) Preparation of the pre-product $C_6F_{13}$$CH_2$—CHI—$CH_2$—$C_6F_{13}$

Proceeding as described in example a), to the 215 grams of the olefin produced in b) 300 grams of $C_6F_{13}$I and 5 grams of azobisisobutyronitrile are added.

After having kept the reactor vessel at 80° C. for 8 hours the whole content is emptied by means of a distillation process under a vacuum of 745 mm Hg until a temperature of 145° C. in the heating vessel is reached. In this manner 53 grams of non-reacted product are obtained in the head as the top product whereas in the heating vessel 460 grams of the desired pre-product remain at a 93 percent purity.

Preparation of the 1,1-2,2(tetrakisperfluorohexyl-methylene)ethane

To the 460 grams of the pre-product obtained in c) 800 cubic centimeters of acid anhydride are added and placed in a spherical vessel equipped with agitator, thermometer, coolant cycle and an opening for adding the zinc in powder form.

The vessel is placed into a thermostatic bath and the feeding in of 45 grams of Zn in powder form is started, while the temperature is being maintained between 35° and 40° C.

After a reaction time of 5 hours the acid anhydride is separated using a separatory funnel from the thick viscous liquid at the bottom which weighs 403 grams.

This liquid is placed into the reactor vessel and 250 cubic centimeters of $H_2O$ and 100 grams of 35% HCl are added, and under agitation, the whole mixture then is brought to boiling in such a manner that the non-reacted zinc is removed and then the whole mixture is transferred into a glass jar and cooled down. From the bottom a solid material is taken (the melting interval of which is 40° to 45° C.) weighing 350 grams.

This solid material is melted and subjected to a fractional distillation process using a column according to Vigreuse at a vacuum of 750 mm Hg. After separation of some top fractions the desired product is distilled between 218° and 222° C.

In this manner 271 grams are obtained containing 95 percent of the desired product the melting point of which is 75° to 76° C.

In the report of the analysis the product is confirmed: I.R., proton N.M.R. (Nuclear Magnetic Resonance) and mass spectrography obtained under electro-spray conditions.

The following are results of sliding tests performed on snow, which demonstrate the gliding properties of the inventive products.

The products designated A and B according to the present invention were applied as ski waxes and their sliding efficiency on the skis was evaluated. In some of these tests the products A and B were used with blends of perfluoroparaffins of high melting points ranging from $C_{16}$ to $C_{24}$, which are perfectly soluble in the tetrakis products of the invention and exhibit the same surface tension.

In this manner the melting point of these blends can be lowered to a maximum of 100° to 105° C. in such a manner that they can be spread onto the ski soles without any danger of parting or deformation of the soles.

Test No. 1

The evaluation of the ski waxes was conducted in the following manner: Two ski champions specialised in this type of tests and equipped with the same type of skis (Stoeckli) first performed two runs with the ski wax of the invention and then, after thorough cleaning of the ski soles, repeated the tests using competitor's ski waxes which are noted as the best commercially available for the type of snow encountered.

The test runs were effected at an attitude of about 1950 meters on winter snow.

On the test piste which was 285 meters long with a level differential of 70 meters several preliminary runs first were performed in such a manner that the snow was compressed.

Before entering the test run piste to be timed chronometrically the test skiers started on a steep slope of a length of 115 meters.

The conditions at the test site were as follows:
Fresh snow
Fair weather
Air temperature −5° C.
Snow temperature −7° C.
Relative humidity 58 percent The ski wax was composed of the compound A.
The test run results are listed in the following table:

|  | 1st test skier | 2nd test skier | Average time | Difference |
|---|---|---|---|---|
| Ski wax | 1st run  2nd | 1st run  2nd | seconds | percent |
| Sample A | 13.62  13.61 | 13.62  13.63 | 13.62 | 0.000 |
| Toko Streamline | 13.62  13.63 | 13.85  13.89 | 13.75 | 0.130 |
| Fluorag. 5 | 13.66  13.67 | 13.77  13.81 | 13.73 | 0.111 |
| Swix FL 200 | 13.69  13.75 | 13.82  13.86 | 13.785 | 0.160 |
| Start FC 33 | 13.62  13.75 | 13.76  13.78 | 13.775 | 0.107 |

Test No. 2

Under the same arrangements as described for the test No. 1 a ski wax consisting of the compound B was tested.

The conditions at the test site were as follows:
Fresh snow
Cloudy weather
Air temperature −11.6° C.
Snow temperature −9.1° C.
Relative humidity 90 percent The test run results are listed in the following table:

|  | 1st test skier | 2nd test skier | Average time | Difference |
|---|---|---|---|---|
| Ski wax | 1st run  2nd | 1st run  2nd | seconds | percent |
| Sample B | 10.79  10.70 | 10.74  10.72 | 10.72 | 0.000 |
| Cold 10 | 10.59  11.77 | 10.86  10.92 | 10.90 | 0.181 |
| Fluorag. 5 | 11.77  10.95 | 11.70  11.15 | 11.44 | 0.720 |
| Cold 9 + Fluorag 5 | 10.90  10.95 | 10.84  10.87 | 10.89 | 0.17 |
| Cold 9 | 10.94  11.05 | 11.06  11.30 | 11.09 | 0.367 |

Test No. 3

Under the same arrangements as described for the test No. 1 a ski wax was tested, consisting of: compound B=70 percent.

The conditions at the test site were as follows:
Settled snow
Fair weather
Air temperature −22° C.
Snow temperature −17° C.
Relative humidity 70 percent The test run results are listed in the following table:

|  | 1st test skier | 2nd test skier | Average time | Difference |
|---|---|---|---|---|
| Ski wax | 1st run  2nd | 1st run  2nd | seconds | percent |
| Test Sample | 11.07  11.01 | 11.00  11.05 | 11.03 | 0.000 |
| Fluorag 5 | 11.77  11.77 | 11.24  11.21 | 11.125 | 0.095 |
| Cold 8 + HPFI | 11.00  11.26 | 11.150  11.16 | 11.144 | 0.114 |
| Artic Plus 2 | 11.21  11.12 | 11.17  11.16 | 11.165 | 0.135 |

What is claimed is:

1. A lubricant for improving the gliding properties of skis and similar items on snow, comprising a compound having four perfluorinated chains attached to a hydrogenated core in such a manner as to form a tetra-substituted derivative according to the formula

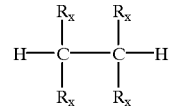

wherein each $R_x$ group can be the same or different and comprises perfluorinated alkyl group.

2. A lubricant according to claim 1, wherein $R_x$ is a group selected from $R_f$, $R_f$—$CH_2$—, or $R_f$—$CH_2$—$CH_2$—, wherein $R_f$ is a perfluorinated alkyl group.

3. A lubricant according to claim 2 wherein $R_f$ is a group selected from $C_4F_9$, $C_6F_{13}$, $C_8F_{17}$, $C_{10}F_{21}$, $C_{12}F_{25}$, and $C_{14}F_{29}$ groups.

4. A lubricant according to claim 1 wherein all the four groups designated $R_x$ are the same.

5. A lubricant according to claim 1 wherein two of the $R_x$ groups are different from the other two $R_x$ groups in the number of carbon atoms.

6. A lubricant according to claim 2 wherein two of the $R_x$ groups are $R_f$ groups, and two of the $R_x$ groups are selected from $R_f$—$CH_2$ and $R_f$—$CH_2$—$CH_2$ groups.

7. A lubricant according to claim 1 comprising, in addition to said compound having four perfluorinated chains attached to a hydrogenated core, blends of high melting point perfluoroparaffins, wherein said perfluoroparaffins comprise from 16 to 24 carbon atoms, and the melting point of the lubricant is less than 105° C.

8. A lubricant according to claim 2, wherein the $R_f$ group is selected from $C_4F_9$, $C_6F_{13}$, $C_8F_{17}$, $C_{12}F_{25}$, and $C_{14}F_{29}$ groups.

9. A lubricant according to claim 2, wherein all the four groups designated $R_x$ are the same.

10. A lubricant according to claim 2, wherein two of the $R_x$ groups are different from the other two $R_x$ groups in the number of carbon atoms.

11. A lubricant according to claim 2, wherein the $R_f$ group contains at least four carbon atoms.

12. A lubricant according to claim 2 comprising, in addition to said compound having four perfluorinated chains attached to a hydrogenated core, a blend of high melting point perfluoroparaffins, wherein said perfluoroparaffins comprise from 16 to 24 carbon atoms, and the melting point of the lubricant is less than 105° C.

13. A lubricant according to claim 3 comprising, in addition to said compound having four perfluorinated chains attached to a hydrogenated core, a blend of high melting point perfluoroparaffins, wherein said perfluoroparaffins comprise from 16 to 24 carbon atoms, and the melting point of the lubricant is less than 105° C.

14. A lubricant according to claim 4 comprising, in addition to said compound having four perfluorinated chains attached to a hydrogenated core, a blend of high melting point perfluoroparaffins, wherein said perfluoroparaffins comprise from 16 to 24 carbon atoms, and the melting point of the lubricant is less than 105° C.

15. A lubricant according to claim 5 comprising, in addition to said compound having four perfluorinated chains attached to a hydrogenated core, a blend of high melting point perfluoroparaffins, wherein said perfluoroparaffins comprise from 16 to 24 carbon atoms, and the melting point of the lubricant is less than 105° C.

16. A lubricant according to claim 6 comprising, in addition to said compound having four perfluorinated chains attached to a hydrogenated core, a blend of high melting point perfluoroparaffins, wherein said perfluoroparaffins comprise from 16 to 24 carbon atoms, and the melting point of the lubricant is less than 105° C.

17. A lubricant according to claim 1 wherein $R_x$ is a perfluorinated alkyl chain.

18. A lubricant according to claim 1 wherein said perfluorinated chains are attached to a hydrogenated core in a symmetrical manner so as to form a tetrakis derivative.

19. A method for endowing skis with improved gliding properties comprising applying the lubricant according to claim 1 to soles of the skis.

20. A method for endowing skis with improved gliding properties comprising applying the lubricant according to claim 7 to soles of the skis.

* * * * *